(12) United States Patent
Kirby et al.

(10) Patent No.: US 6,734,143 B2
(45) Date of Patent: May 11, 2004

(54) 2-METHOXYIMINO-2 (PYRIDINYLOXYMETHYL)PHENYL ACETAMIDES USEFUL AS FUNGICIDES

(75) Inventors: Neil Vincent Kirby, Carmel, IN (US); Jenifer Lynn Adamski Butz, Avon, IN (US); Brent Jeffrey Rieder, Greenfield, IN (US); James M. Renga, Indianapolis, IN (US); Jeannie Rachel Phillips Cetusic, Avon, IN (US); Irene Mae Morrison, Indianapolis, IN (US); John Todd Mathieson, Brownsburg, IN (US); Gary David Gustafson, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/363,024

(22) PCT Filed: Sep. 19, 2001

(86) PCT No.: PCT/US01/29352

§ 371 (c)(1),
(2), (4) Date: Feb. 27, 2003

(87) PCT Pub. No.: WO02/24688

PCT Pub. Date: Mar. 28, 2002

(65) Prior Publication Data

US 2004/0063763 A1 Apr. 1, 2004

Related U.S. Application Data

(60) Provisional application No. 60/233,738, filed on Sep. 19, 2000.

(51) Int. Cl.$^7$ .......................... A01N 43/86; A01N 43/82; C07D 413/04

(52) U.S. Cl. .................. 504/223; 504/251; 504/252; 504/253; 504/248; 504/236; 504/239; 504/244; 544/63; 544/96; 544/228; 544/333; 546/271.4; 546/272.4; 546/274.1; 546/275.4; 546/276.4; 546/194; 546/269.4; 514/340; 514/336; 514/341; 514/343; 514/348; 514/228.8

(58) Field of Search .................. 546/271.4, 272.1, 546/272.4, 274.1, 275.4, 276.4, 194; 544/96, 63, 228, 333; 504/223, 251, 252, 253, 248, 236, 239

(56) References Cited

U.S. PATENT DOCUMENTS

| | | | |
|---|---|---|---|
| 5,852,013 A | 12/1998 | Gerdes et al. | 514/224.2 |
| 6,114,363 A | 9/2000 | Oberdorf et al. | 514/345 |
| 6,133,294 A | 10/2000 | Kirby et al. | 514/340 |
| 6,211,202 B1 | 4/2001 | Canada et al. | 514/336 |

FOREIGN PATENT DOCUMENTS

| | | |
|---|---|---|
| EP | 0738716 | 10/1996 |
| EP | 0811614 | 12/1997 |

*Primary Examiner*—Evelyn Mei Huang
(74) *Attorney, Agent, or Firm*—Carl D. Corvin; Lynn M. Zettler

(57) ABSTRACT

The present invention provides 2-methoxyimino-2-(pyridinyloxymethyl) phenyl acetamides according to formula (I) as well as their use as fungicidal compounds.

16 Claims, No Drawings

2-METHOXYIMINO-2 (PYRIDINYLOXYMETHYL)PHENYL ACETAMIDES USEFUL AS FUNGICIDES

PRIORITY

This application is a 371 of PCT/US 01/29352, which claims priority from U.S. provisional application serial number 60/233,738, which was filed on Sep. 19, 2000. The entire disclosure of this provisional application is hereby incorporated by reference.

FIELD OF THE INVENTION

This invention is related to the field of compounds having fungicidal activity and processes to make and use such compounds.

BACKGROUND OF THE INVENTION

Our history is riddled with outbreaks of fungal diseases that have caused widespread human suffering. One need look no further than the Irish potato famine of the 1850's, where an estimated 1,000,000 people died, to see the effects of a fungal disease.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield of the crop and consequently, increase the value of the crop. In most situations, the increase in value of the crop is worth at least three times the cost of the use of the fungicide. However, no one fungicide is useful in all situations.

Consequently, research is being conducted to produce fungicides that are safer, that have better performance, that are easier to use, and that cost less. In light of the above, the inventors provide this invention.

SUMMARY OF THE INVENTION

It is an object of this invention to provide compounds that have fungicidal activity. It is an object of this invention to provide processes that produce compounds that have fungicidal activity. It is an object of this invention to provide processes that use compounds that have fungicidal activity. In accordance with this invention, processes to make and processes to use compounds having a general formula according to formula one, and said compounds are provided.

While all the compounds of this invention have fungicidal activity, certain classes of compounds may be preferred for reasons such as, for example, greater efficacy or ease of synthesis.

DETAILED DESCRIPTION OF THE INVENTION

The compounds have a formula according to formula one. In formula one:

Formula One

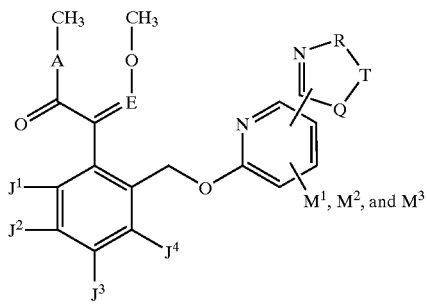

A is selected from the group consisting of oxy (—O—) and amino (—NH—);

E is selected from the group consisting of aza (—N═) and methine (—CH═);

$j^1, j^2, j^3$, and $J^4$ are independently selected from the group consisting of hydro (—H), halo (—F, —Cl, —Br, and —I), $C_{1-4}$ alkyl, $C_{1-4}$ alkoxy, $C_{1-4}$ alkyl (mono or multi-halo), and $C_{1-4}$ alkylthio;

$M^1, M^2$, and $M^3$ are selected from the group consisting of hydro (—H), halo (—F, —Cl, —Br, and —I), $C_{1-4}$ alkyl, $Cl_4$ alkoxy, $C_{1-4}$ alkyl (mono or multi-halo), and $C_{1-4}$ alkylthio, nitro (—NO$_2$), (mono or multi-halo) $C_{1-4}$ alkoxy;

Q is selected from the group consisting of oxy (—O—), NX (where X is selected from the group consisting of hydro (—H) and $C_{1-4}$ alkyl, or X is the connecting bond to the pyridyl), and $CZ^1 Z^2$ (where each Z is independently selected from the group consisting of hydro (—H) and $C_{1-4}$ alkyl, or one Z is the connecting bond to the pyridyl);

R is selected from the group consisting of oxy (—O—), $NX^1$ (where $X_1$ is selected from the group consisting of hydro (—H) and $C_{1-4}$ alkyl, or $X^1$ is the connecting bond to the pyridyl), and $CZ^3 Z^4$ (where each Z is independently selected from the group consisting of hydro (—H) and $C_{1-4}$ alkyl, or one Z is the connecting bond to the pyridyl); and T is a $C_{1-2}$ carbon atom chain connecting Q to R where each carbon atom in this chain is fully saturated. Consequently, each carbon atom in the chain in T has four other single bonds. T can be optionally substituted with a $C_{1-4}$ alkyl or one of the single bonds can be the connecting bond to the pyridyl.

The term "alkyl", "alkenyl", or "alkynyl" refers to an unbranched or branched chain carbon group. The term "alkoxy" refers to an unbranched or branched chain alkoxy group. The term "haloalkyl" refers to an unbranched or branched alkyl group substituted with one or more halo atoms. The term "haloalkoxy" refers to an alkoxy group substituted with one or more halo atoms. Throughout this document, all temperatures are given in degrees Celsius and all percentages are weight percentages, unless otherwise stated. The term "Me" refers to a methyl group. The term "Et" refers to an ethyl group. The term "Pr" refers to a propyl group. The term "Bu" refers to a butyl group. The term "EtOAc" refers to ethyl acetate. The term "ppm" refers to parts per million. The term, "psi" refers to pounds per square inch.

In general, these compounds can be used in a variety of ways. These compounds are preferably applied in the form of a formulation comprising one or more of the compounds with a phytologically acceptable carrier. Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of one or more of the compounds.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present invention contemplates all vehicles by which one or more of the compounds can be formulated for delivery and use as a fungicide.

As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds, an inert carrier and surfactants. The concentration of the compound in the wettable powder is usually from about 10% to about 90% w/w, more preferably about 25% to about 75% w/w. In the preparation of wettable powder formulations, the compounds can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the compounds in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Usefully organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 50% w/w. Suspensions are prepared by finely grinding one or more of the compounds, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds may also be applied as granular formulations, which are particularly useful for applications to the soil. Granular formulations usually contain from about 0.5% to about 10% w/w of the compounds, dispersed in an inert carrier which consists entirely or in large part of coarsely divided attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. Such formulations may also be prepared by making a dough or paste of the carrier and the compound, and crushing and drying to obtain the desired granular particle.

Dusts containing the compounds are prepared simply by intimately mixing one or more of the compounds in powdered form with a suitable dusty agricultural carrier, such as, for example, kaolin clay, ground volcanic rock, and the like. Dusts can suitably contain from about 1% to about 10% w/w of the compounds.

The formulations may contain adjuvant surfactants to enhance deposition, wetting and penetration of the compounds onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5%. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that can comprise at least 1% of one or more of the compounds with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds and the pesticidal compound in the combination can generally be present in a weight ratio of from 1:100 to 100:1

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds. The compounds are suitable for treatment of various plants at fungicidal levels, while exhibiting low phytotoxicity. The compounds are useful in a protectant or eradicant fashion. The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi that infect useful plant crops. Activity has been demonstrated for a variety of fungi, including for example the following representative fungi species:

Downy Mildew of Grape (*Plasmopara viticola*—PLASVI);
Late Blight of Tomato (*Phytophthora infestans*—PHYTIN);
Apple Scab (*Venturia inaequalis*—VENTIN);
Brown Rust of Wheat (*Puccinia recondita*—PUCCRT);
Stripe Rust of Wheat (*Puccinia striiformis*—PUCCST);
Rice Blast (*Pyricularia oryzae*—PYRIOR);
Cercospora Leaf Spot of Beet (*Cercospora beticola*—CERCBE);
Powdery Mildew of Wheat (*Erysiphe graminis*—ERYSGT);
Leaf Blotch of Wheat (*Septoria tritici*—SEPTTR);
Sheath Blight of Rice (*Rhizoctonia solani*—RHIZSO);
Eyespot of Wheat (*Pseudocercosporella herpotrichoides*—PSDCHE);
Brown Rot of Peach (*Monilinia fructicola*—MONIFC); and
Glume Blotch of Wheat (*Septoria nodorum*—LEPTNO).

It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

EXAMPLES

These examples are provided to further illustrate the invention. They are not meant to be construed as limiting the invention.

5,6-Dichloro-pyridine-3-aldehyde, oxime

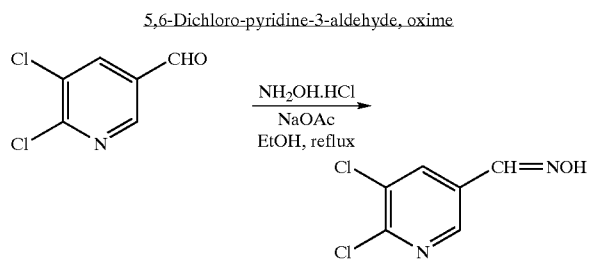

A mixture of 5,6-dichloro-pyridine-3-aldehyde (3.0 g, 0.017 mol), anhydrous sodium acetate (3.0 g, 0.037 mol), hydroxylamine hydrochloride (2.0 g, 0.029 mol) and ethanol (50 mL) was heated with stirring under reflux conditions for 3 hours. The mixture was cooled to room temperature, poured into water (250 mL) and filtered. The resulting white solid was dissolved in dichloromethane (200 mL), and the solution dried over anhydrous sodium sulphate. Evaporation of the solvent under reduced pressure and recrystallization of the residue from ethyl acetate gave the desired product (2.90 g, 89%) as a white solid, melting point. 150–2° C.

5,6-Dichloro-N-hydroxy-3-pyridinecarboximidoyl chloride

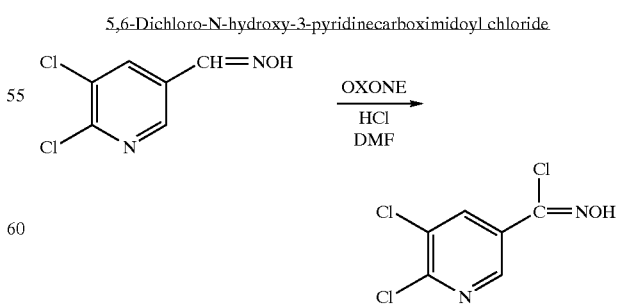

5,6-Dichloro-pyridine-3-aldehyde, oxime (0.96 g, 5 mmol) was dissolved with stirring in a 0.5M solution of hydrogen chloride in DMF (11 mL), and OXONE□ (1.69 g, 2.75 mmol) added. The mixture was stirred for 5 hours, additional OXONE (0.85 g, 1.38 mmol) added, and the mixture stirred overnight. It was poured into ice water, and the resultant solid collected by filtration and dried. Recrystallization from ethyl acetate: hexane gave the desired product (0.97 g, 86%) as a white solid, melting point. 185–6° C.

3-(2,3-Dichloro-5-pyridyl)-5,5-dimethyl-4,5-dihydroisoxazole

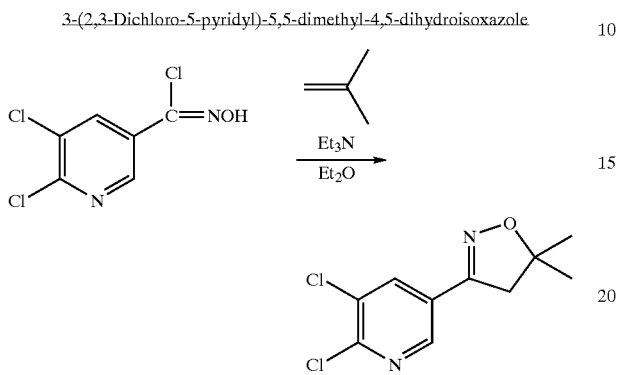

5,6-Dichloro-N-hydroxy-3-pyridinecarboximidoyl chloride (1.0 g, 4.5 mmol) was dissolved with stirring in ether (50 mL) and a solution of triethylamine (1.0 g, 10 mmol) in ether (50 mL) added dropwise to the solution while isobutylene was bubbled through the reaction mixture. The mixture was stirred at room temperature overnight, filtered, and the filtrate evaporated to dryness under reduced pressure. Recrystallization of the residue from hexane gave the desired product (0.73 g, 66%) as a cream solid, melting point. 91–3° C.

3-(3-Chloro-2-methylthio-5-pyridyl)-5,5-dimethyl-4,5-dihydroisoxazole

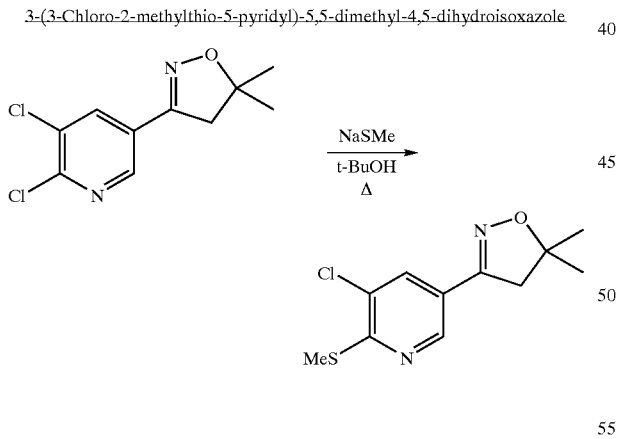

3-(2,3-Dichloro-5-pyridyl)-5,5-dimethyl-4,5-dihydroisoxazole (0.60 g, 2.4 mmol) was dissolved in t-butanol (25 mL) and sodium methanethiolate (0.21 g, 3.0 mmol) added. The reaction mixture was heated at 45° C. with stirring for 3 hours, cooled, and poured onto ice. The resulting cream precipitate was collected by filtration, dissolved in dichloromethane (50 mL), and dried over anhydrous sodium sulphate. Evaporation of the solvent under reduced pressure gave the desired product (0.50 g, 81%) as a cream solid.

3-(3-Chloro-2-methylsulphonyl-5-pyridyl)-5,5-dimethyl-4,5-dihydroisoxazole

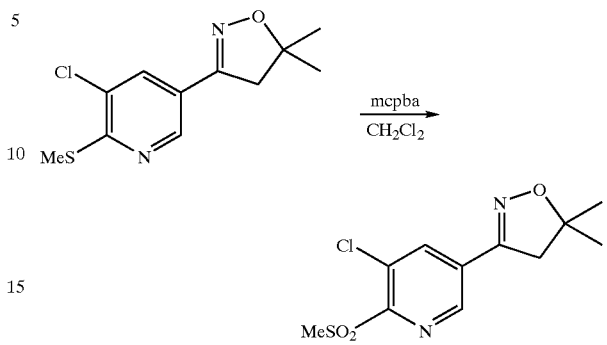

3-(3-Chloro-2-methylthio-5-pyridyl)-5,5-dimethyl4,5-dihydroisoxazole (0.56 g, 2.2 mmol) was dissolved with stirring in dichloromethane (50 mL) and m-chloroperoxybenzoic acid (1.40 g, 60% assay, 4.9 mmol) added. The mixture was stirred at room temperature for 4 hours and 10% sodium carbonate solution (50 mL) added. The mixture was separated and the organic phase washed three times with 2M sodium hydroxide solution (50mL) and brine. It was dried over anhydrous sodium sulphate and evaporated under reduced pressure to give the desired product as a clear oil that solidifies on standing (0.58 g, 90%).

Benzeneacetamide,2-[[[3-chloro-5-(5,5-dimethyl-4,5-dihydroisoxazolyl)-2-pyridinyl]oxy]methyl-α-(methoxyimino)-N-methyl-

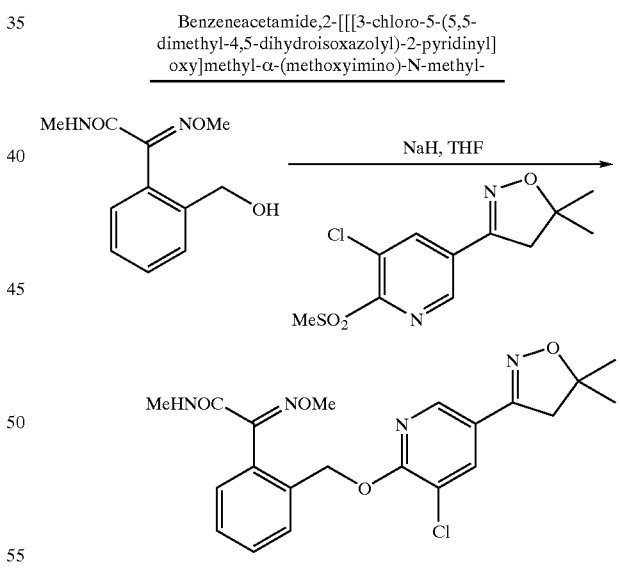

Compound Three 2-(Hydroxymethyl)-a-(methoxyimino)-N-methylbenzeneacetamide (0.42 g, 1.9 mmol) was dissolved with stirring in anhydrous THF (20 mL) and 60% sodium hydride (0.14 g, 3.46 mmol) added. The mixture was stirred at room temperature for 30 minutes and a solution of 3-(3-chloro-2-methylsulphonyl-5-pyridyl)-5,5-dimethyl4, 5-dihydroisoxazole (0.5 g, 1.74 mmol) in anhydrous THF (15 mL) added. The resultant mixture was heated at 50° C. with stirring for 4 hours, cooled, and poured into water. It was then extracted twice with ethyl acetate (50 mL), the organic extracts combined, and washed with water (50 mL) and brine (50 mL). It was dried over anhydrous sodium sulphate, evaporated to dryness under reduced pressure, and the residue purified by chromatography over silica (5–40% ethyl acetate: hexane) to give the desired product (0.55 g, 68%) as a clear oil, which solidifies on standing.

5,6-Dichloropyridine-5-carboxamide;N-(2-hydroxy-1,1,-dimethylethyl)-

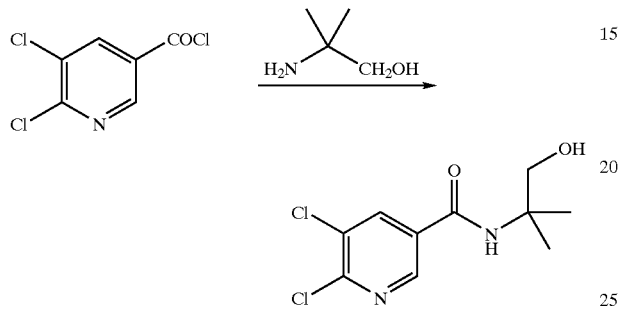

A mixture of 2-amino-2-methyl-propan-1-ol (2.11 g, 0.024 mol) and triethylamine (4.8 g, 0.048 mol) in dichloromethane (50 mL) was stirred and cooled to 0° C. A solution of 5,6-dichloronicotinoyl chloride (2.5 g, 0.012 mol) in dichloromethane (25 mL) was added dropwise and the mixture stirred overnight. Water (25 mL) was added and the mixture separated. The organic phase was washed with 10% sodium carbonate solution (50 mL), water (25 mL), 2M hydrochloric acid (50 mL), and brine (50 mL). It was then dried over anhydrous sodium sulphate and evaporated under reduced pressure to give the desired compound (2.72 g, 86%) as a pale orange oil.

2-(5,6-Dichloro-3-pyridyl)-5-,5-dimethyl-4,5-dihydrooxazole

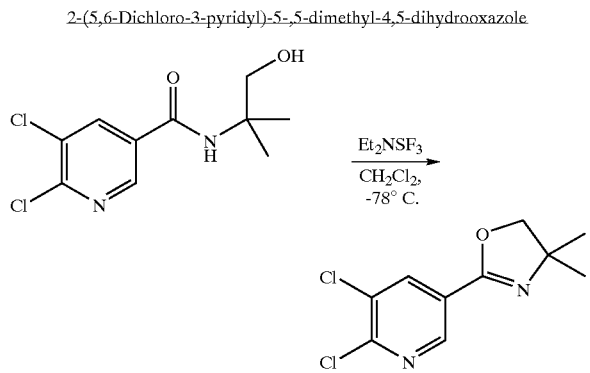

N-(2-Hydroxy-1, 1, -dimethylethyl)-5,6-dichloropyridine-5-carboxamide (0.50 g, 1.90 mmol) was dissolved with stirring in dichloromethane (20 mL) and cooled to −78° C. Diethylaminosulphur trifluoride (0.34 g, 2.12 mmol) was added dropwise and the mixture stirred at −78° C. for one hour. The mixture was quenched at low temperature with 4M ammonium hydroxide solution (20 mL) and warmed to room temperature. The mixture was separated and the solvent evaporated under reduced pressure to give a tan oil. Purification of this oil by reverse phase HPLC (70:30 acetonitrile: water) gave the desired product (0.44 g, 94%) as a clear oil which crystallizes on standing.

2-(5-Chloro-6-methylthio-3-pyridyl)-5,5-dimethyl-4,5-dihydrooxazole

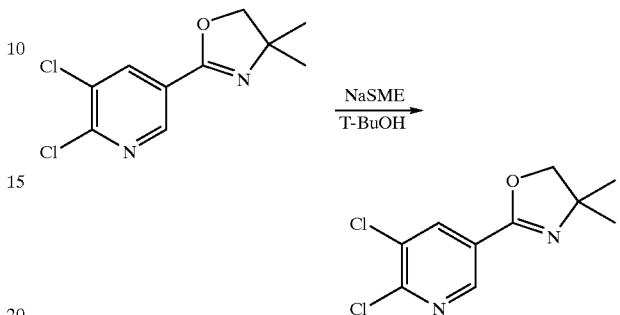

2-(5,6-Dichloro-3-pyridyl)-5,5-dimethyl4, 5-dihydrooxazole (2.0 g, 8.2 mmol) was dissolved with stirring in t-butanol (40 mL) and sodium methanethiolate (0.69 g, 9.80 mmol) added. The mixture was stirred at 60° C. for six hours, cooled to room temperature, and poured into water. The mixture was extracted with dichloromethane (50 mL) and the organic phase washed with water (50 mL) and brine (50 mL), and dried over anhydrous sodium sulphate. Evaporation of the solvent under reduced pressure gave the desired product as a cream solid (1.3 g, 62%), m. pt. 113–5° C.

2-(5-Chloro-6-methylsulphonyl-3-pyridyl)-5,-dimethyl-4,5-dihydrooxazole

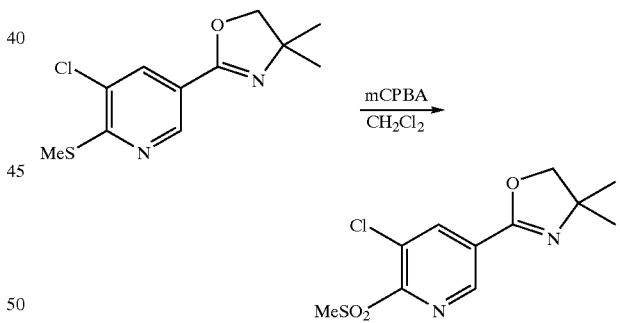

2-(5-Chloro-6-methylthio-3-pyridyl)-5,5-dimethyl-4, 5-dihydrooxazole (1.0g, 3.7 mmol) was dissolved with stirring in dichloromethane (50 mL) and m-chloroperoxybenzoic acid (2.36 g, 60% assay, 8.2 mmol) added. The mixture was stirred overnight, 10% sodium carbonate solution (50 mL) added, and the mixture stirred for one hour. This was separated and the organic phase washed twice with 2M sodium hydroxide solution (30 mL) and with brine (25 mL). Drying over anhydrous sodium sulphate and evaporation of the solvent under reduced pressure gave the desired product (0.9 g, 80%) as a white solid, m. pt 102–5° C.

Benzeneacetamide,2-[[[3-chloro-5-(5,5-dimethyl-4,5-dihydro-2-oxazolyl)-2-pyridinyl]oxy]methyl-α-(methoxyimino)-N-methyl-

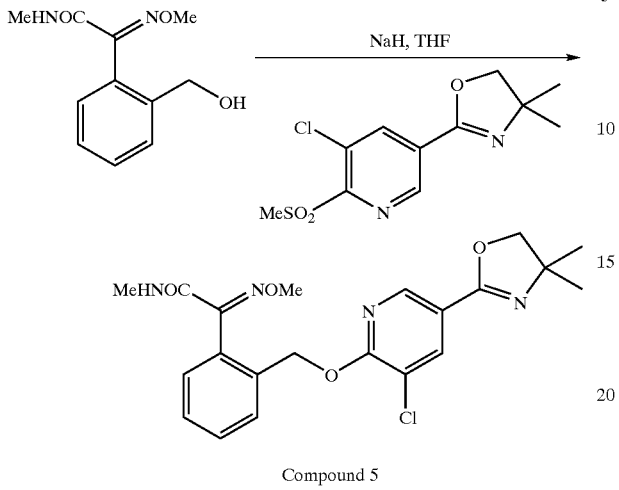

Compound 5

2-(Hydroxymethyl)-α-(methoxyimino)-N-methylbenzeneacetamide (0.32 g, 1.45 mmol) was dissolved with stirring in anhydrous THF (20 mL) and 60% sodium hydride (0.12 g, 3.0 mmol) added. The mixture was stirred at room temperature for 30 minutes and a solution of 2-(5-chloro-6-methylsulphonyl-3-pyridyl)-5,5-dimethyl-4,5-dihydrooxazole (0.4 g, 1.39 mmol) in anhydrous THF (15 mL) added. The resultant mixture was heated at 50° C. with stirring for 4 hours, cooled, and poured into water. It was then extracted twice with ethyl acetate (50 mL), the organic extracts combined, and washed with water (50 mL) and brine (50 mL). It was dried over anhydrous sodium sulphate, evaporated to dryness under reduced pressure, and the residue purified by chromatography over silica (10–50% ethyl acetate: hexane) to give the desired product (0.35 g, 58%) as a white solid, melting point. 145–7° C.

5,6-Dichloropyridine-5-carboxamide;N-(3-hydroxy-1,1,-dimethylethyl)

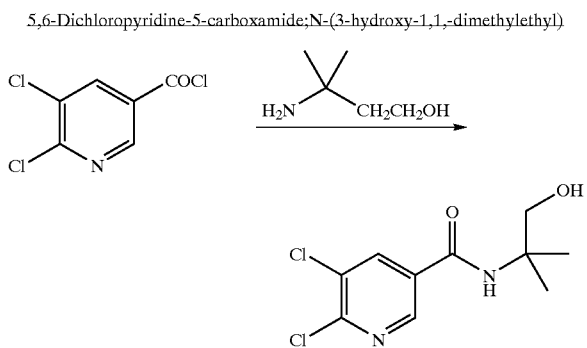

A mixture of 3-amino-3-methyl-butan-1-ol (0.98 g, 9.45 mmol) and aqueous 1N sodium hydroxide (30 ml) in dichloromethane (20 mL) was stirred. A solution of 5,6-dichloronicotinoyl chloride (2.0 g, 9.45 mmol) in dichloromethane (20 mL) was added dropwise and the mixture stirred overnight. The mixture was neutralized with 1N HCl and it was poured into water. It was then extracted three times with dichloromethane (25 mL). The organic extracts were combined and washed twice with water (50 mL) and once with brine (50 mL). It was dried over anhydrous sodium sulphate, filtered, and evaporated to dryness under reduced pressure to give the desired compound (1.08 g, 41%) as a yellow sticky solid.

2-(5,6-Dichloro-3-pyridyl)-4,4-dimethyl-5,6-dihydrooxazine

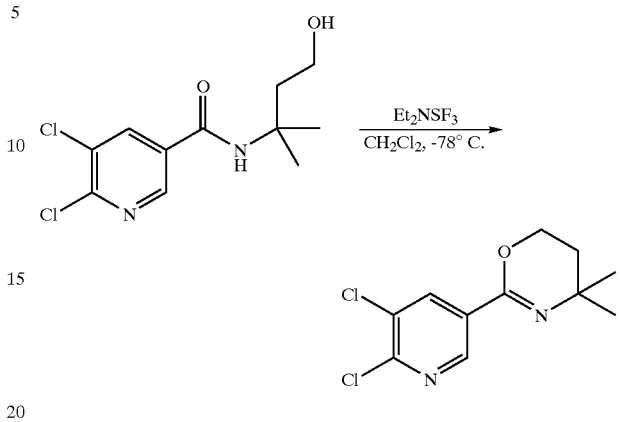

N-(3-Hydroxy-1,1,-dimethylethyl)-5,6-dichloropyridine-5-carboxamide (0.50 g, 1.80 mmol) was dissolved with stirring in dichloromethane (20 mL) and cooled to −78° C. Diethylaminosulphur trifluoride (0.26 ml, 1.98 mmol) was added dropwise and the mixture stirred at −78° C. for one hour. The mixture was quenched at low temperature with 4M ammonium hydroxide solution (10 mL), warmed to room temperature, and stirred overnight. The mixture was poured into water (25 ml) and extracted free times with dichloromethane (25 ml). The organic extracts were combined and washed once with water (50 ml) and once with brine (50 ml). It was dried over sodium sulfate, filtered, and evaporated under reduced pressure to dryness. The residue was purified by chromatography over silica (25–50% ethyl acetate: hexane) to give the desired product as a yellow crystalline solid (0.27 g, 59%).

Benzeneacetamide, 2-[[[3-chloro-5-(4,4-dimethyl-5,6-dihydro-2-oxazinyl)-2-pyridinyl]oxy]methyl-α-(methoxyimino)-N-methyl-

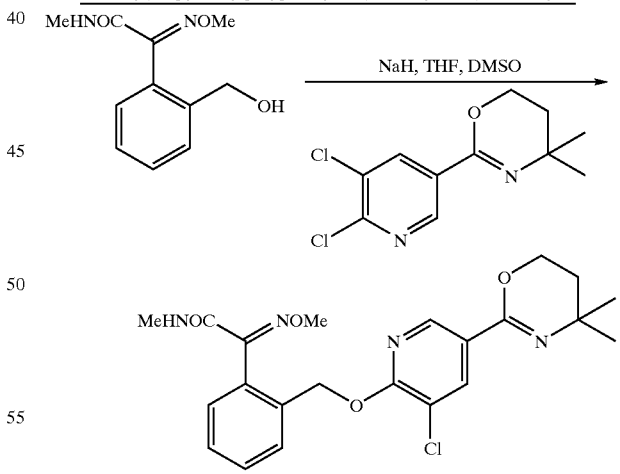

Compound Six 2-(Hydroxymethyl)-☐-(methoxyimino)-N-methylbenzeneacetamide (0.14 g, 0.637 mmol) was dissolved with stirring in anhydrous THF (25 mL) and 60% sodium hydride (32 mg, 0.810 mmol) added. The mixture was stirred at room temperature for 15 minutes and 2-(5,6-dichloro-3-pyridyl)4,4-dimethyl-5, 6-dihydrooxazine (0.15 g, 0.579 mmol) was added. The resultant mixture was heated at 50° C. with stirring for 3 hours, cooled, and stirred at room temperature overnight. Anhydrous dimethylsulfoxide (1 ml) was added and the mixture was reheated to 50° C. with stirring for 3 hours and cooled to room temperature. The mixture was quenched with water (15 ml) and extracted three times with ethyl acetate (25 mL). The organic extracts were combined, washed twice with water (25 mL), and once with brine (30 mL). It was dried over anhydrous sodium sulphate, filtered, and evaporated to dryness under reduced pressure. The residue purified by chromatography over silica (20–50% ethyl acetate: hexane) to give the desired product (35 mg, 14%) as a clear oil.

5,6-Dichloropyridine-5-carboxamide; N-(4-hydroxy-2-butyl)-

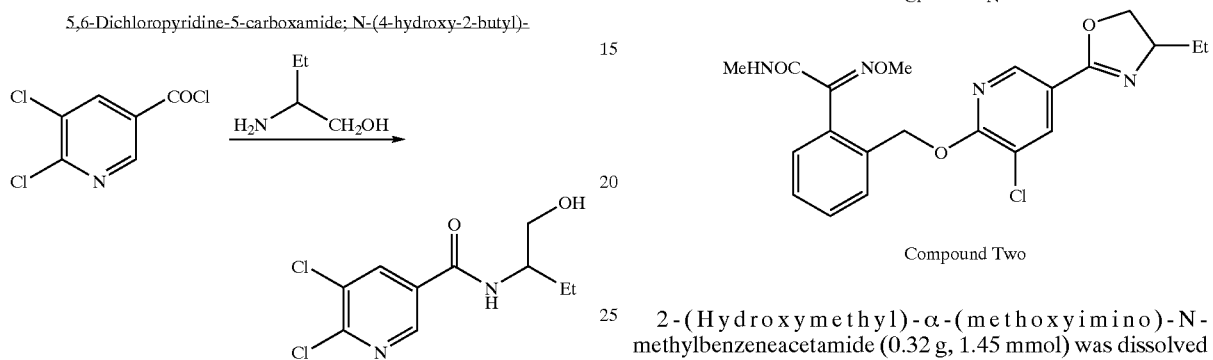

A mixture of 2-amino-butan-1-ol (2.11 g, 0.024 mol) and triethylamine (4.8 g, 0.048 mol) in dichloromethane (50 mL) was stirred and cooled to 0° C. A solution of 5,6-dichloronicotinoyl chloride (2.5 g, 0.012 mol) in dichloromethane (25 mL) was added dropwise and the mixture stirred overnight. Water (25 mL) was added and the mixture separated. The organic phase was washed with 10% sodium carbonate solution (50 mL), water (25 mL), 2M hydrochloric acid (50 mL) and brine (50 mL). It was then dried over anhydrous sodium sulphate and evaporated under reduced pressure to give the desired compound (1.99 g, 63%) as a tan solid, melting point 107–9° C.

2-(5,6-Dichloro-3-pyridyl)-5-ethyl-4,5-dihydrooxazole

N-(4-hydroxy-2-butyl)-5,6-dichloropyridine-5-carboxamide (0.50 g, 1.90 mmol) was dissolved with stirring in dichloromethane (20 mL) and cooled to −78° C. Diethylaminosulphur trifluoride (0.34 g, 2.12 mmol) was added dropwise and the mixture stirred at −78° C. for one hour. The mixture was quenched at low temperature with 4M ammonium hydroxide solution (20 mL) and warmed to room temperature. The mixture was separated and the solvent evaporated under reduced pressure to give a tan oil. Purification by chromatography over silica (0–10% ethyl acetate: pentane) gave the desired product (0.42 g, 90%) as a clear oil.

Benzeneacetamide, 2-[[[3-chloro-5-(5-ethyl-4,5-dihydro-2-oxazolyl)-2-pyridinyl]oxy]methyl-α-(methoxyimino)-N-methyl-

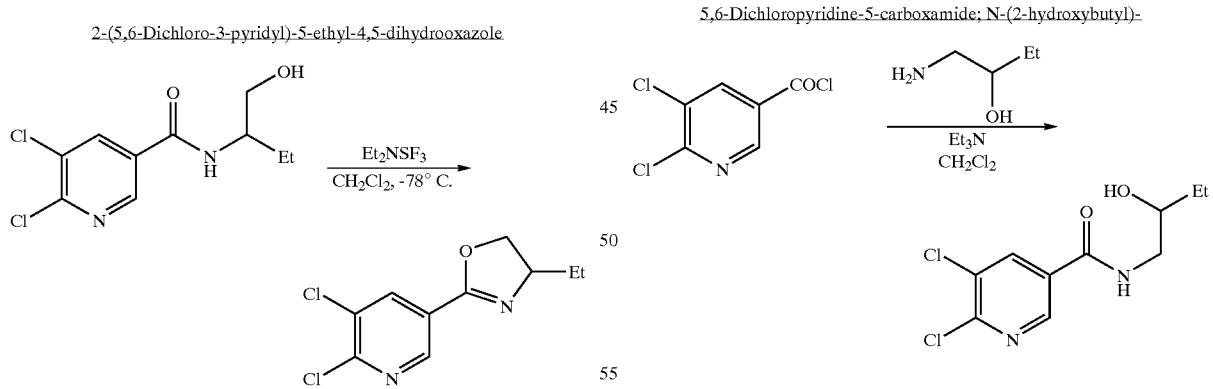

Compound Two 2-(Hydroxymethyl)-α-(methoxyimino)-N-methylbenzeneacetamide (0.32 g, 1.45 mmol) was dissolved with stirring in anhydrous THF (20 mL) and 60% sodium hydride (0.12 g, 3.0 mmol) added. The mixture was stirred at room temperature for 30 minutes and a solution of 2-(5,6-dichloro-3-pyridyl)-5-ethyl-4,5-dihydrooxazole (0.4 g, 1.39n-mol) in anhydrous THF (15 mL) added. The resultant mixture was heated at 50° C. with stirring for 4 hours, cooled, and poured into water. It was then extracted twice with ethyl acetate (50 nL), the organic extracts combined, and washed with water (50 mL) and brine (50 mL). It was dried over anhydrous sodium sulphate, evaporated to dryness under reduced pressure, and the residue purified by chromatography over silica (10–50% ethyl acetate: hexane) to give the desired product (0.42 g, 70%) as a clear oil.

5,6-Dichloropyridine-5-carboxamide; N-(2-hydroxybutyl)-

A mixture of 2-hydroxybutylamine (2.11 g, 0.024 mol) and triethylamine (4.8 g, 0.048 mol) in dichloromethane (50 mL) was stirred and cooled to 0° C. A solution of 5,6-dichloronicotinoyl chloride (2.5 g, 0.012 mol) in dichloromethane (25 mL) was added dropwise and the mixture stirred overnight. Water (25 mL) was added and the mixture separated. The organic phase was washed with 10% sodium carbonate solution (50 mL), water (25 mL), 2M hydrochloric acid (50 mL) and brine (50 mL). It was then dried over anhydrous sodium sulphate and evaporated under reduced pressure to give the desired compound (2.70 g, 85%) as a white solid, melting point 128–31° C.

2-(5,6-Dichloro-3-pyridyl)-4-ethyl-4,5-dihydrooxazole

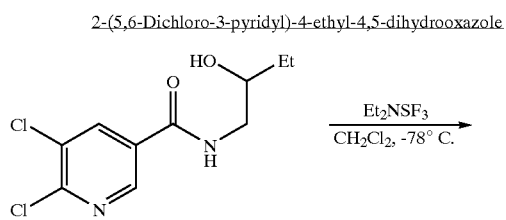

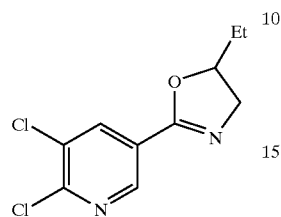

N-(2-Hydroxybutyl)-5,6-dichloropyridine-5-carboxamide (0.50 g, 1.90 mmol) was dissolved with stirring in dichloromethane (20 mL) and cooled to −78° C. Diethylaminosulphur trifluoride (0.34 g, 2.12 mmol) was added dropwise and the mixture stirred at −78° C. for one hour. The mixture was quenched at low temperature with 4M ammonium hydroxide solution (20 mL) and warmed to room temperature. The mixture was separated and the solvent evaporated under reduced pressure to give a tan oil. Purification of this oil by chromatography over silica (5–30% ethyl acetate: hexane) gave the desired product (0.45 g, 96%) as a clear oil.

2-(5-Chloro-6-methylthio-3-pyridyl)-4-ethyl-4,5-dihydrooxazole

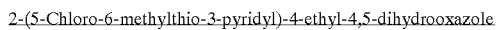

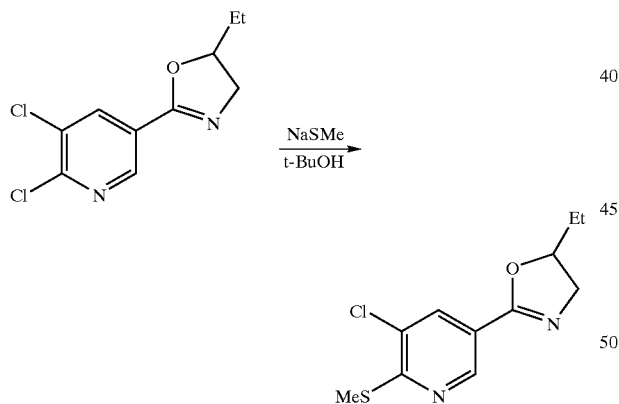

2-(5,6-Dichloro-3-pyridyl)4ethyl-4,5-dihydrooxazole (2.0 g, 8.2 mmol) was dissolved with stirring in t-butanol (40 mL) and sodium methanethiolate (0.69 g, 9.80 mmol) added. The mixture was stirred at 60° C. for six hours, cooled to room temperature, and poured into water. The mixture was extracted with dichloromethane (50 mL) and the organic phase washed with water (50 mL) and brine (50 mL), and dried over anhydrous sodium sulphate. Evaporation of the solvent under reduced pressure gave the desired product as a yellow oil (2.4 g, 91%).

2-(5-Chloro-6-methylsulphonyl-3-pyridyl)-4-ethyl-4,5-dihydrooxazole

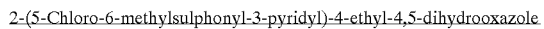

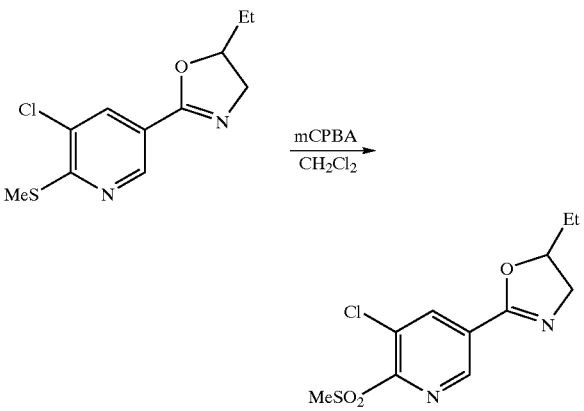

2-(5-Chloro-6-methylthio-3-pyridyl)4ethyl-4,5-dihydrooxazole (1.0 g, 3.7 mmol) was dissolved with stirring in dichloromethane (50 mL) and m-chloroperoxybenzoic acid (2.36 g, 60% assay, 8.2 mmol) added. The mixture was stirred overnight, 10% sodium carbonate solution (50 mL) added, and the mixture stirred for one hour. This was separated and the organic phase washed twice with 2M sodium hydroxide solution (30 mL) and with brine (25 mL). Drying over anhydrous sodium sulphate and evaporation of the solvent under reduced pressure gave the desired product (0.9 g, 80%) as a clear oil which solidifies on standing.

Benzeneacetamide, 2-[[[3-chloro-5-(4-ethyl-4,5-dihydro-2-oxazolyl)-2-pyridinyl]oxy]methyl-α-(methoxyimino)-N-methyl-

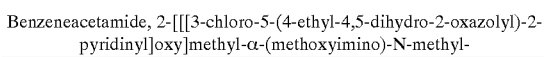

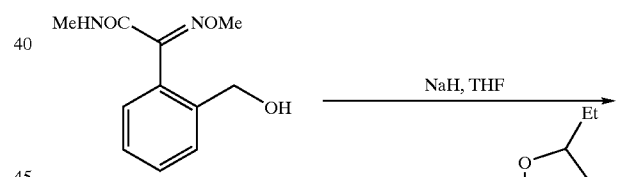

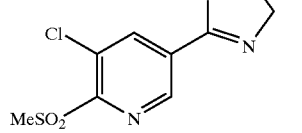

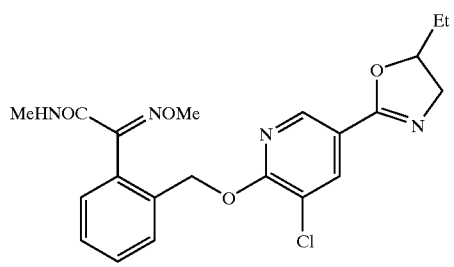

Compound 4

2-(Hydroxymethyl)-α-(methoxyimino)-N-methylbenzeneacetamide (0.32 g, 1.45 mmol) was dissolved with stirring in anhydrous THF (20 mL) and 60% sodium hydride (0.12 g, 3.0 mmol) added. The mixture was stirred at room temperature for 30 minutes and a solution of 2-(5-chloro-6-methylsulphonyl-3-pyridyl)4-10 ethyl-4,5-dihydrooxazole (0.4 g, 1.39 mmol) in anhydrous THF (15 mL) added. The resultant mixture was heated at 50° C. with stirring for 4 hours, cooled, and poured into water. It was then extracted twice with ethyl acetate (50 mL), the organic extracts combined, and washed with water (50 mL) and brine (50 mL). It was dried over anhydrous sodium sulphate, evaporated to dryness under reduced pressure, and the residue purified by chromatography over silica (10–50% ethyl acetate: hexane) to give the desired product (0.42 g, 70%) as an oily solid.

(2E)-2-[2-({[5-(4,5-dihydroisoxazol-3-yl)-3-methylpyridin-2-yl]oxy} methyl)phenyl]-2-(methoxyimino)-N-methylethanamide Compound One A mixture of (2E)-2-[2-(hydroxymethyl)phenyl]-2-(methoxyimino)-N-methylethanamide (80 mg, 0.36 mmol) and sodium hydride (60% suspension in mineral oil; 15 mg, 0.37 mmol) in anhydrous tetrahydrofuran (2 mL) under nitrogen was stirred for 2 minutes at ambient temperature, then a solution of 5-(4,5-dihydroisoxazol-3-yl)-2-fluoro-3-methylpyridine (60 mg, 0.33 mmol) in anhydrous tetrahydrofuran (3 mL) was added, and the mixture was stirred for 18 hours. TLC analysis showed one major new component ($R_f$=0.44, $CH_2Cl_2$-EtOAc 2:1). The mixture was partitioned between ether (30 mL) and saturated aqueous $NH_4Cl$ (10 mL), and the organic phase was washed with water and brine, dried ($MgSO_4$), filtered and concentrated under vacuum. Chromatography of the residue on a preparative plate of silica gel (20×20 cm, 2 mm thickness), eluting with $CH_2Cl_2$-EtOAc 2:1, afforded 78 mg (63%) of the desired title compound as a white solid. Spectral data were consistent with the assigned structure.

BIOLOGICAL RESULTS

The compounds were formulated at 100 ppm in 10% acetone plus 0.01% Triton X100 and tested for efficacy at the whole plant level in a 1-day protectant test (1DP). Chemicals were sprayed on a turn table sprayer fitted with two opposing air atomization nozzles which delivered approximately 1500 L/ha of spray volume. Disease severity was evaluated 1 to 3 weeks later.

Compound Formulation: Compound formulation was accomplished by dissolving technical materials in acetone, with serial dilutions then made in acetone to obtain desired rates. Final treatment volumes were obtained by adding nine volumes 0.05% aqueous Tween-20 or Triton X-100, depending upon the pathogen.

Late Blight of Tomatoes (*Phytophthora infestans*—PHYTMN): Tomatoes (*cultivar Rutgers*) were grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Phytophthora infestans*. The plants were then transferred to the greenhouse until disease developed on the untreated control plants.

Powdery Mildew of Wheat (*Erysiphe graminis*—ERYSGT): Wheat (*cultivar Monon*) was grown in a soilless peat-based potting mixture (Metromix) until the seedlings were 1–2 leaf (BBCH 12). These plants were then sprayed to run off with the test compound at a rate of 100 ppm. After 24 hours the test plants were inoculated with *Erysiphe graminis* by dusting spores from stock plants onto the test plants. The plants were then transferred to the greenhouse until disease developed on the untreated control plants.

Glume blotch of wheat (*Leptosphaeria nodorum*—LEPTNO): Wheat (*cultivar Monon*) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Leptosphaeria nodorum*. The plants were then transferred to the greenhouse until disease developed on the untreated control plants.

Brown rust (*Puccinia recondita*—PUCCRT): Wheat (*cultivar Monon*) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Puccinia recondita*. The plants were then transferred to the greenhouse until disease developed on the untreated control plants.

The following table presents the activity of typical compounds of the present invention when evaluated in these experiments. The effectiveness of the test compounds in controlling disease was rated by giving the percent control of the plant disease.

TABLE ONE
"BIOLOGICAL DATA FOR COMPOUNDS 1–6"
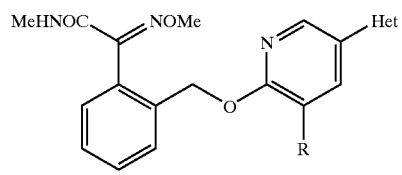
| Compound Number | R | Het | ERYSGT 1DP | LEPTNO 1DP | PHYTIN 1DP | PUCCRT 1DP |
|---|---|---|---|---|---|---|
| 1 | Me | 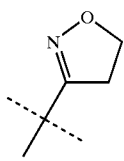 | >95 | ? | >95 | >95 |
| 2 | Cl | 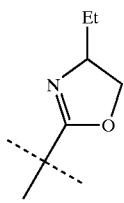 | >95 | >80 | <50 | >95 |
| 3 | Cl | 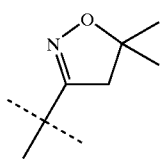 | >95 | <50 | <50 | >95 |
| 4 | Cl | 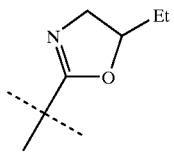 | >80 | >95 | <50 | >95 |

TABLE ONE-continued

"BIOLOGICAL DATA FOR COMPOUNDS 1–6"

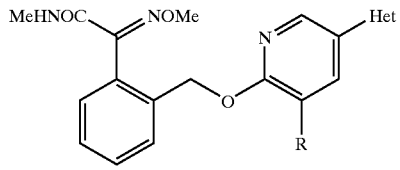

| Compound Number | R | Het | ERYSGT 1DP | LEPTNO 1DP | PHYTIN 1DP | PUCCRT 1DP |
|---|---|---|---|---|---|---|
| 5 | Cl | 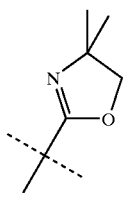 | >80 | >95 | <50 | >95 |
| 6 | Cl | 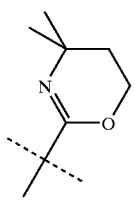 | >80 | >95 | <50 | >95 |

? = Not tested

?=Not tested

What is claimed is:

1. A compound according to formula one

Formula One

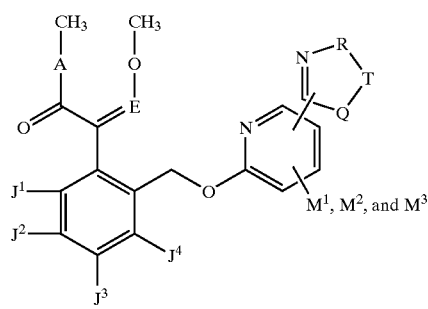

wherein

A is selected from the group consisting of oxy (—O—) and amino (—NH—);

E is selected from the group consisting of aza (—N═) and methine (—CH═);

$j^1$, $j^2$, $j^3$, and $j^4$ are independently selected from the group consisting of hydro (—H), halo (—F, —Cl, —Br, and —I), $C_{1-4}$ alkyl, $C_{1-4}$ alkoxy, $C_{1-4}$ alkyl (mono or multi-halo), and $C_{1-4}$ alkylthio;

$M^1$, $M^2$, and $M^3$ are selected from the group consisting of hydro (—H), halo (—F, —Cl, —Br, and —I), $C_{1-4}$ alkyl, $C_{1-4}$ alloxy, $C_{1-4}$ alkyl (mono or multi-halo), and $C_{1-4}$ alkylthio, nitro (—NO$_2$), (mono or multi-halo) $C_{1-4}$ alkoxy;

Q is selected from the group consisting of oxy (—O—), NX (where X is selected from the group consisting of hydro (—H) and $C_{1-4}$ alkyl, or X is the connecting bond to the pyridyl), and $CZ^1 Z^2$ (where each Z is independently selected from the group consisting of hydro (—H) and $C_{1-4}$ alkyl, or one Z is the connecting bond to the pyridyl);

R is selected from the group consisting of oxy (—O—), $NX^1$ (where $X^1$ is selected from the group consisting of hydro (—H) and $C_{1-4}$ alkyl, or $X^1$ is the connecting bond to the pyridyl), and $CZ^3 Z^4$ (where each Z is independently selected from the group consisting of hydro (—H) and $C_{1-4}$ alkyl, or one Z is the connecting bond to the pyridyl); and T is a $C_{1-2}$ carbon atom chain connecting Q to R where each carbon atom in this chain is fully saturated.

2. A compound according to claim 1 wherein A is amino (—NH—).

3. A compound according to claim 1 wherein E is aza (—N=).

4. A compound according to claim 1 wherein $J^1$, $J^2$, $J^3$, and $J^4$ are hydro (—H).

5. A compound according to claim 1 wherein $M^1$, $M^2$, and $M^3$ are selected from the group consisting of hydro (—H), halo (—F, —Cl, —Br, and —I), and $C_{1-4}$ alkyl.

6. A compound according to claim 1 wherein Q is selected from the group consisting of oxy (—O—), and $CZ^1Z^2$ (where each Z is independently selected from the group consisting of hydro (—H) and $C_{1-4}$ alkyl, or one Z is the connecting bond to the pyridyl).

7. A compound according to claim 1 wherein R is selected from the group consisting of oxy (—O—), and $CZ^3Z^4$ (where each Z is independently selected from the group consisting of hydro (—H) and $C_{1-4}$ alkyl, or one Z is the connecting bond to the pyridyl).

8. A compound according to claim 1 wherein A is amino (—NH—); E is aza (—N=); $J^1$, $J^2$, $J^3$, and $J^4$ are hydro (—H); $M^1$, $M^2$, and $M^3$ are selected from the group consisting of hydro (—H), halo (—F, —Cl, —Br, and —I), and $C_{1-4}$ alkyl; Q is selected from the group consisting of oxy (—O—), and $CZ^1Z^2$ (where each Z is independently selected from the group consisting of hydro (—H) and $C_{1-4}$ alkyl, or one Z is the connecting bond to the pyridyl); and R is selected from the group consisting of oxy (—O—), and $CZ^3Z^4$ (where each Z is independently selected from the group consisting of hydro (—H) and $C_{1-4}$ alkyl, or one Z is the connecting bond to the pyridyl).

9. A process comprising applying a fungicidal amount of a compound according to claim 1 to a locus to control or prevent a fungal attack.

10. A process comprising applying a fungicidal amount of a compound according to claim 2 to a locus to control or prevent a fungal attack.

11. A process comprising applying a fungicidal amount of a compound according to claim 3 to a locus to control or prevent a fungal attack.

12. A process comprising applying a fungicidal amount of a compound according to claim 4 to a locus to control or prevent a fungal attack.

13. A process comprising applying a fungicidal amount of a compound according to claim 5 to a locus to control or prevent a fungal attack.

14. A process comprising applying a fungicidal amount of a compound according to claim 6 to a locus to control or prevent a fungal attack.

15. A process comprising applying a fungicidal amount of a compound according to claim 7 to a locus to control or prevent a fungal attack.

16. A process comprising applying a fungicidal amount of a compound according to claim 8 to a locus to control or prevent a fungal attack.

* * * * *